US006626842B2

(12) United States Patent
Oka (10) Patent No.: US 6,626,842 B2
(45) Date of Patent: Sep. 30, 2003

(54) HEART-SOUND ANALYZING APPARATUS (75) Inventor: Tohru Oka, Ichinomiya (JP)

(73) Assignee: Colin Corporation, Komaki (JP)

( * ) Notice: Subject to any disclaimer, the term of this patent is extended or adjusted under 35 U.S.C. 154(b) by 334 days.

(21) Appl. No.: 09/822,426

(22) Filed: Apr. 2, 2001

(65) Prior Publication Data
US 2002/0035337 A1 Mar. 21, 2002

(30) Foreign Application Priority Data

Aug. 9, 2000  (JP) ........................................ 2000-241703

(51) Int. Cl.[7] .......................... A61B 5/0205; A61B 7/04
(52) U.S. Cl. ...................... 600/528; 600/526; 600/529
(58) Field of Search ................................ 600/485, 486, 600/508, 509, 513, 526, 528, 529, 586, 514; 607/6

(56) References Cited

U.S. PATENT DOCUMENTS

| 4,928,690 | A | * | 5/1990 | Heilman et al. | ............ | 600/509 |
| 5,178,151 | A | * | 1/1993 | Sackner | ...................... | 600/485 |
| 6,120,442 | A | * | 9/2000 | Hickey | ........................ | 600/486 |
| 6,238,349 | B1 | * | 5/2001 | Hickey | ........................ | 600/486 |
| 6,440,079 | B1 | * | 8/2002 | Ogura et al. | ................. | 600/485 |
| 6,477,405 | B1 | * | 11/2002 | Kawaguchi | ................. | 600/513 |

FOREIGN PATENT DOCUMENTS

| EP | 1179317 A2 | * | 2/2002 |
| EP | 1279370 A1 | * | 1/2003 |

* cited by examiner

Primary Examiner—Willis R. Wolfe
(74) Attorney, Agent, or Firm—Oliff & Berridge, PLC (57) ABSTRACT A heart-sound analyzing apparatus, including a heart-sound microphone which is adapted to be worn on a living subject to iteratively detect a second heart sound II of the subject, a respiration-synchronous-signal detecting device which iteratively detects a respiration-synchronous signal of the subject, an inspiration-expiration judging device for judging, based on each of the respiration-synchronous signals iteratively detected by the respiration-synchronous-signal detecting device, whether the subject is in an inspiring state or in an expiring state, and an aortic-valve-closing-timing determining device for iteratively determining a timing when the aortic valve of the heart of the subject closes, based on each of second heart sounds II which are iteratively detected by the heart-sound microphone in time intervals, respectively, in each of which the subject is judged as being in the inspiring state by the inspiration-expiration judging device.

7 Claims, 6 Drawing Sheets

HEART-SOUND ANALYZING APPARATUS

BACKGROUND OF THE INVENTION

1. Field of the Invention

The present invention relates to a heart-sound analyzing apparatus which can determine a timing when aortic valve closes, and particularly to such an apparatus which can iteratively determine a timing when aortic valve closes.

2. Related Art Statement

A second heart sound II includes a component resulting from closure of aortic valve. For a certain diagnosis, it is useful to determine a timing when aortic valve closes. For example, a timing of closure of aortic valve may be utilized to measure a pulse-wave propagation velocity PWV at which a pulse wave propagates in a living subject. Pulse-wave propagation velocity PWV can be determined by dividing a propagation time DT needed for a pulse wave to propagate between two reference positions, by a propagation distance between the two reference positions. Therefore, as propagation time DT increases, an accuracy of determination of propagation velocity PWV increases. Since the closure of aortic valve occurs at the upstream-side end of blood flow, the distance of propagation of pulse wave can be increased by determining the timing of closure of aortic valve, and accordingly a highly accurate propagation velocity PWV can be determined based on the increased propagation distance. In addition, since the ejection of blood from the heart ends with the closure of aortic valve, the timing of closure of aortic valve needs to be determined to calculate an ejection time.

The second heart sound II includes not only the component IIA resulting from the closure of aortic valve but also a component IIP resulting from closure of pulmonary valve. Though, generally, the component IIP follows the component IIA, a time interval between the component IIA and the component IIP is changed by respiration of a subject. More specifically described, the above-indicated time interval is increased and the two components IIA, IIP are separated from each other, when the subject is inspiring, but the time interval is decreased and the first half portion of the component IIP overlaps the second half portion of the component IIA, when the subject is expiring. Though the component IIA needs to be analyzed to determine the timing of closure of aortic valve, it is difficult to analyze the component IIA overlapped by the component IIP. To solve this problem, it has conventionally been practiced to ask the subject to control his or her respiration.

However, it is difficult for a subject to control continuously his or her respiration for the purpose of determining iteratively a timing of closure of aortic valve. In particular, it is difficult for a patient under a surgical operation to control continuously his or her respiration.

SUMMARY OF THE INVENTION

It is therefore an object of the present invention to provide a heart-sound analyzing apparatus which can accurately and iteratively determine a timing when aortic valve closes.

The above object has been achieved by the present invention. According to a first feature of the present invention, there is provided a heart-sound analyzing apparatus, comprising a heart-sound microphone which is adapted to be worn on a living subject to iteratively detect a second heart sound II of the subject; a respiration-synchronous-signal detecting device which iteratively detects a respiration-synchronous signal of the subject; an inspiration-expiration judging means for judging, based on each of the respiration-synchronous signals iteratively detected by the respiration-synchronous-signal detecting device, whether the subject is in an inspiring state or in an expiring state; and an aortic-valve-closing-timing determining means for iteratively determining a timing when an aortic valve of a heart of the subject closes, based on each of a plurality of second heart sounds II which are iteratively detected by the heart-sound microphone in a plurality of time intervals, respectively, in each of which the subject is judged as being in the inspiring state by the inspiration-expiration judging means.

In the present heart-sound analyzing apparatus, the inspiration-expiration judging means judges, based on each of the respiration-synchronous signals detected by the respiration-synchronous-signal detecting device, whether the living subject is in an inspiring state or in an expiring state, and the aortic-valve-closing-timing determining means determines a timing when the aortic valve closes, based on a second heart sound II which is detected by the heart-sound microphone when the subject is in the inspiring state. Therefore, the present apparatus can accurately and iteratively determine a timing when the aortic valve closes, without needing to force the subject to control his or her respiration.

According to a second feature of the present invention, the aortic-valve-closing-timing determining means determines a timing when the aortic valve closes, based on the last one of a plurality of second heart sounds II which are detected by the heart-sound microphone in each of the plurality of time intervals in each of which the subject is judged as being in the inspiring state by the inspiration-expiration judging means. In the present heart-sound analyzing apparatus, the aortic-valve-closing-timing determining means determines a timing when the aortic valve closes, based on the last second heart sound II wherein the component IIA and the component IIP are most largely separated from each other. Therefore, the present apparatus can more accurately determine a timing when the aortic valve closes.

According to a third feature of the present invention, the heart-sound analyzing apparatus further comprises a smoothing means for smoothing, by differentiation, a waveform of the second heart sounds iteratively detected by the heart-sound microphone; and a squaring means for squaring respective amplitudes of a plurality of data points on the smoothed waveform that are determined with respect to a base line of the smoothed waveform, and the aortic-valve-closing-timing determining means iteratively determines a timing when the aortic valve closes, based on the amplitudes squared by the squaring means. Each of the second heart sounds II detected by the heart-sound microphone includes a low-frequency noise, and has an alternating waveform including positive amplitudes and negative amplitudes on both sides of a base line thereof. In the present heart-sound analyzing apparatus, the smoothing means smoothes, by differentiation, a waveform of the second heart sounds detected by the heart-sound microphone, and thereby provides a smoothed waveform in the form of a differentiated waveform which shows a clear change of amplitudes. In addition, the squaring means squares respective amplitudes of respective data points on the smoothed waveform that are determined with respect to a base line of the smoothed waveform, and thereby provides a squared waveform having the thus squared amplitudes on only the positive side of the base line. And, the aortic-valve-closing-timing determining means determines a timing when the aortic valve closes, based on the squared waveform provided by the squaring means. Therefore, the present apparatus can determine a more accurate timing when the aortic valve closes.

According to a fourth feature of the present invention, the heart-sound analyzing apparatus further comprises an electrocardiograph which includes a plurality of electrodes adapted to be worn at a plurality of locations on the subject and which detects, through the electrodes, an electrocardiogram of the subject, and the aortic-valve-closing-timing determining means comprises means for iteratively determining, based on a prescribed point of each of respective first half portions of a plurality of T-waves of the electrocardiogram detected by the electrocardiograph, a start point of a corresponding one of a plurality of waveform-process intervals in each of which the aortic-valve-closing-timing determining means is to seek a timing when the aortic valve closes. A second heart sound II occurs during a certain time duration around the second half portion of each T-wave of the electrocardiogram. Therefore, the present heart-sound analyzing apparatus identifies, as the component IIA, the first change of the waveform of the second heart sound II after the start point of each waveform-process interval, and does not erroneously identify a different change as the component IIA. Thus, the present apparatus can more accurately determine a timing when the aortic valve closes.

According to a fifth feature of the present invention, there is provided a system for obtaining information relating to a propagation velocity at which a pulse wave propagates along an artery of a living subject, the system comprising a heart-sound analyzing apparatus according to any one of the above-described first to fourth features; a pulse-wave detecting device which is adapted to be worn on the subject to detect the pulse wave which propagates along the artery of the subject; and a pulse-wave-propagation-velocity-relating-information obtaining means for obtaining the information based on the timing when the aortic valve closes, determined by the aortic-valve-closing-timing determining means of the heart-sound analyzing apparatus, and a timing when a prescribed point of the pulse wave is detected by the pulse-wave detecting device.

The information relating to the pulse-wave propagation velocity may be the pulse-wave propagation velocity itself, or a pulse-wave propagation time.

In the present pulse-wave-propagation-velocity-relating-information obtaining system, the aortic-valve-closing-timing determining means of the heart-sound analyzing apparatus accurately determines a timing when the aortic valve closes, and the pulse-wave-propagation-velocity-relating-information obtaining means obtains the pulse-wave-propagation-velocity-relating information, based on the accurately determined timing when the aortic valve closes, and a timing when the prescribed portion of the pulse wave is detected by the pulse-wave detecting device. Therefore, the present system can obtain accurate pulse-wave-propagation-velocity-relating information.

BRIEF DESCRIPTION OF THE DRAWINGS

The above and optional objects, features, and advantages of the present invention will be better understood by reading the following detailed description of preferred embodiments of the invention when considered in conjunction with the accompanying drawings, in which.

DETAILED DESCRIPTION OF PREFERRED EMBODIMENTS

Figure 1:
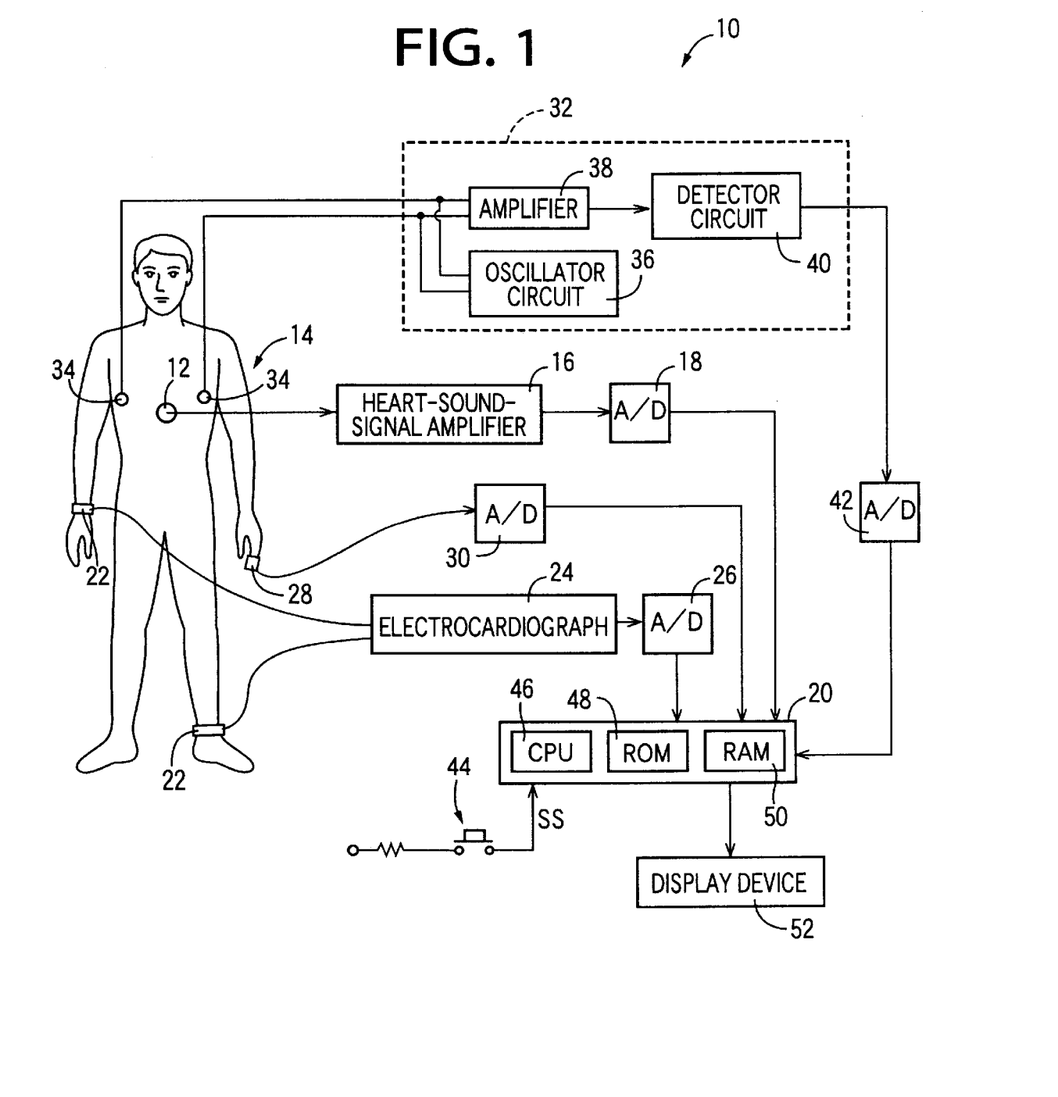
FIG. 1 is a diagrammatic view for explaining a construction of a pulse-wave-propagation-velocity-relating-information obtaining system including a heart-sound analyzing apparatus, to which the present invention is applied.

Hereinafter, there will be described an embodiment of the present invention, by reference to the drawings. FIG. 1 is a diagrammatic view for explaining the construction of a pulse-wave-propagation-velocity-relating-information obtaining system 10 functioning as a heart-sound analyzing apparatus, to which the present invention is applied.

In FIG. 1, the present system 10 includes an acceleration-type heart-sound microphone 12 which is fixed, with an adhesive tape, not shown, to a prescribed location (e.g., the left end of the fourth intercostal sternum, the left end of the second intercostal sternum, the right end of the second intercostal sternum, or the right end of the fourth intercostal sternum) on a chest of a living subject 14 who is taking a face-up position. The microphone 12 accommodates a piezoelectric element, not shown, which converts heart sounds produced from the heart of the subject 14, into an electric signal, i.e., heart-sound signal SH. A heart-sound signal amplifier 16 includes four sorts of filters, not shown, which cooperate with one another to attenuate a low-pitch component having a great energy and thereby amplifies and filters a high-pitch component of the heart-sound signal SH. The heart-sound signal SH output from the amplifier 16 is supplied to an electronic control device 20 via an analog-to-digital (A/D) converter 18.

An electrocardiograph 24 includes two electrodes 22 which are adapted to be worn on respective body portions of the subject 14 that are distant from each other via the heart, and which cooperate with each other to provide an electrocardiogram signal SE representing an action potential of the cardiac muscle of the subject 14. In the present embodiment, the two electrodes 22 are worn on a right wrist and a left ankle of the subject 14, respectively, to provide a two-electrode-induced electrocardiogram. The electrocardiogram signal SE produced from the electrodes 22 is amplified by an amplifier, not shown, of the electrocardiograph 24, and then is supplied to the control device 20 via an A/D converter 26.

Figure 2:
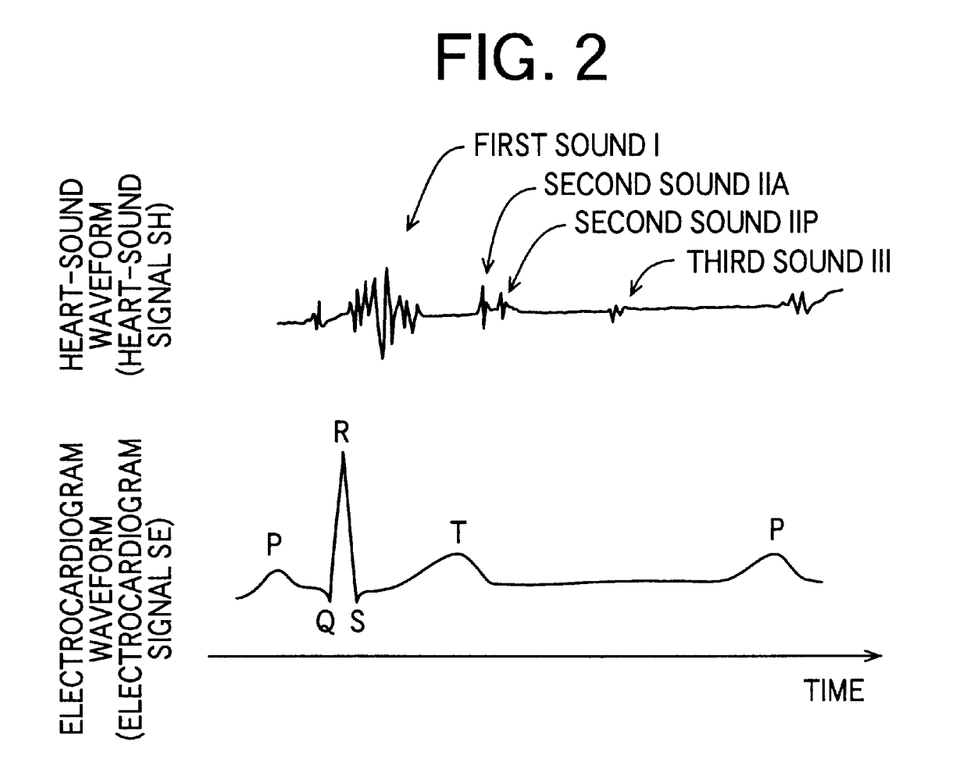
FIG. 2 is a graph showing an electrocardiogram and a heart-sound wave which are detected by an electrocardiograph and a microphone of the system of FIG. 1.

FIG. 2 shows a waveform of the heart sounds detected by the microphone 12, and a waveform of the electrocardiogram detected by the electrocardiograph 24. As shown in FIG. 2, a second heart sound II may be detected such that a sound component IIA and a sound component IIP are clearly separated from each other.

A photoelectric-pulse-wave sensor 28 functions as a pulse-wave detecting device which detects a pulse wave propagated to peripheral arterioles including capillaries, and may have a construction similar to that of one which is used to detect pulse. The sensor 28 is worn on a body portion (e.g., an end portion of a finger) of the subject 14. The sensor 28 includes a housing, not shown, which can accommodate a body portion of the subject 14; a light emitting element, not shown, as a light source which emits, toward a skin of the subject 14, a red or infrared light in such a wavelength band that can be reflected by hemoglobin, preferably a light having a wavelength of about 800 nm that is not influenced by blood oxygen saturation; and a light receiving element, not shown, which detects the light scattered from the body portion under the skin. The sensor 28 outputs a photoelectric-pulse-wave signal SM representing respective instantaneous volumes of the blood present in the capillaries of the body portion, and supplies the signal SM to the control device 20 via an A/D converter 30. The photoelectric-pulse-wave signal SM changes or pulsates in synchronism with each heartbeat of the subject 14, and represents the instantaneous amount of the hemoglobin present in the capillaries of the body portion under the skin, i.e., the volume of the blood present in the capillaries.

A thoracic-impedance detecting device 32 functioning as a respiration-synchronous-signal detecting device detects change of an impedance of a thorax of the subject 14, including lungs, and includes two electrodes 34 adapted to be worn on respective locations on the chest of the subject 14. The detecting device 32 detects, through the two electrodes 34, a thoracic-impedance pulse wave, and outputs a thoracic-impedance signal SI representing the detected thoracic-impedance pulse wave, to the control device 20 via an A/D converter 42. The detecting device 32 includes an oscillator circuit 36 which generates a sinusoidal current having a prescribed frequency (e.g., 50 kHz) and applies the sinusoidal current to the subject 14; an amplifier 38 which amplifies a signal obtained through the electrodes 34; and a detector circuit 40 which extracts, from the amplified signal, the thoracic-impedance signal SI representing the thoracic-impedance pulse wave.

A push button 44 supplies, when being pushed by an operator, a start signal SS to the control device 20.

The control device 20 is essentially provided by a so-called microcomputer including a central processing unit (CPU) 46, a read only memory (ROM) 48, a random access memory (RAM) 50, an input-and-output (I/O) port, not shown, etc. The control device 20 or the CPU 46 processes signals according to control programs pre-stored in the ROM 50, while utilizing a temporary-storage function of the RAM 48, and thereby iteratively determines a timing when the aorta valve of the heart of the subject 14 closes, and iteratively obtains a piece of pulse-wave-propagation-velocity-relating information. In addition, the CPU 46 operates a display device 52 to display iteratively the obtained pulse-wave-propagation-velocity-relating information.

Figure 3:
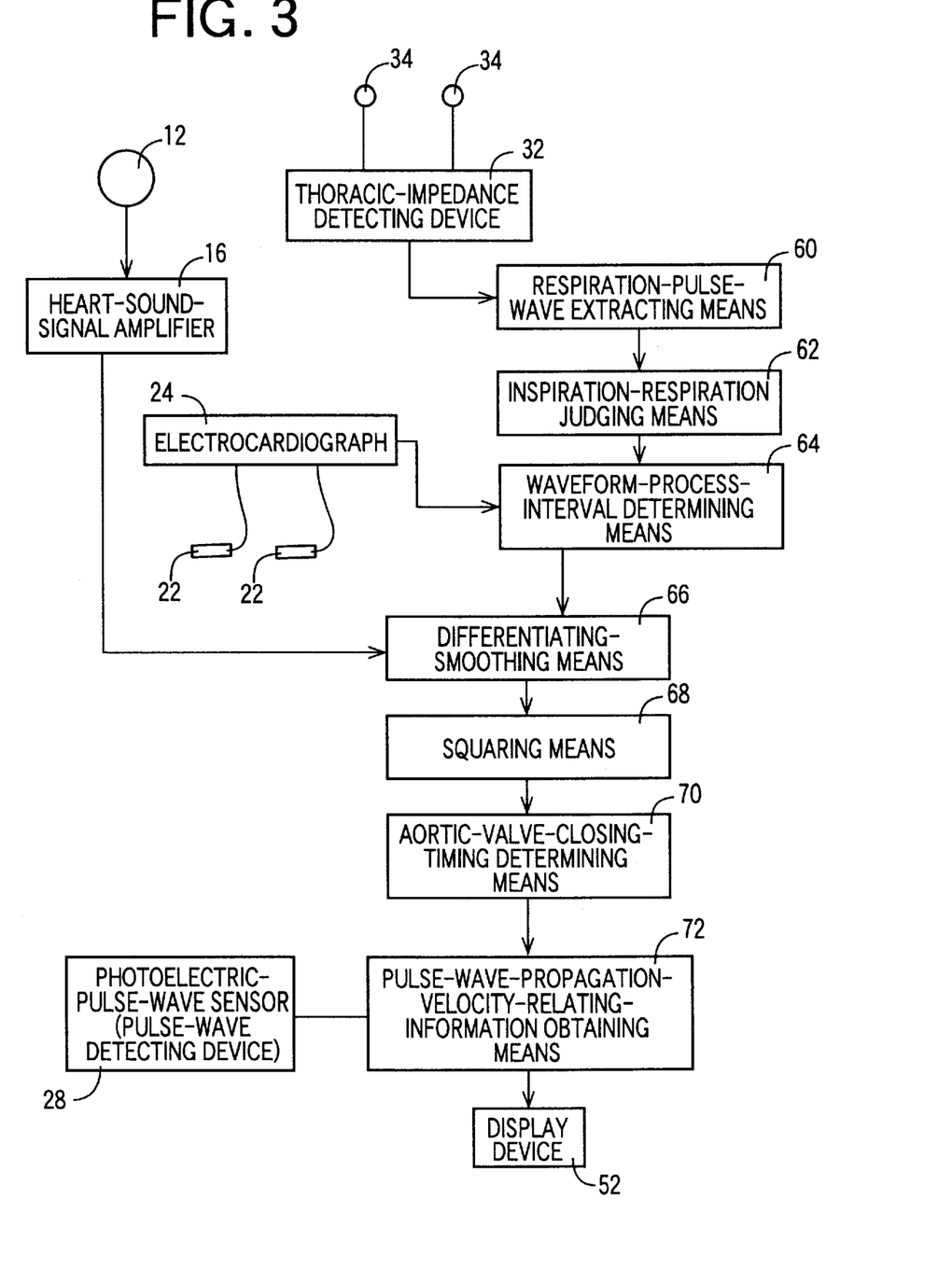
FIG. 3 is a block diagram for explaining essential functions of an electronic control device of the system of FIG. 1.
Figure 4A:
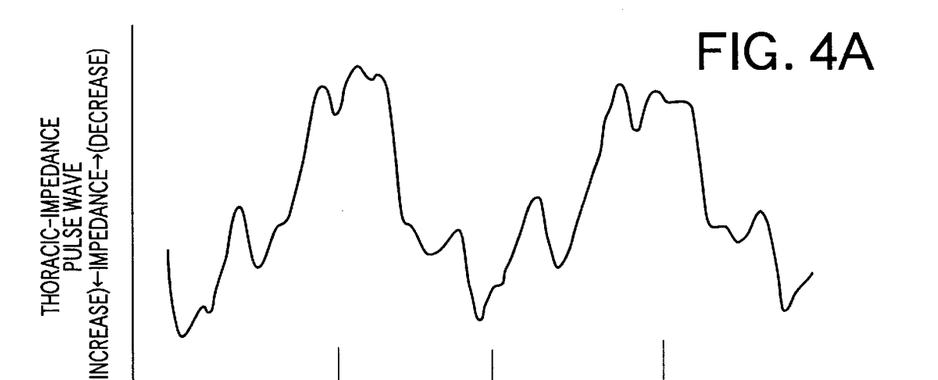
FIG. 4A is a graph showing a thoracic-impedance pulse wave which is detected by a thoracic-impedance detecting device of the system of FIG. 1.

FIG. 3 is a block diagram for explaining essential functions of the control device 20 of the information obtaining system 10. In the figure, a respiration-pulse-wave extracting means 60 successively extracts, from the thoracic-impedance signal SI supplied from the thoracic-impedance detecting device 32, a respiration pulse wave consisting of respiration-synchronous pulses. FIG. 4A shows a thoracic-impedance pulse wave represented by the thoracic-impedance signal SI, and the thoracic-impedance pulse wave includes a heartbeat-synchronous wave representing the change of volume of blood present in the heart, shown in FIG. 4C, and a respiration-synchronous wave or respiration pulse wave representing the change of volume of air present in the thorax, shown in FIG. 4B. Thus, the respiration-pulse-wave extracting means 60 functions as a pulse-wave separating means for separating, from the thoracic-impedance signal SI, a respiration-synchronous component, i.e., a respiration pulse wave having a frequency in a frequency band of from 0.1 to 0.5 Hz. In each of FIGS. 4A and 4B, the vertical axis of each graph indicates that impedance decreases in an upward direction along the axis; and in FIG. 4C, the vertical axis of the graph indicates that impedance increases in an upward direction along the axis.

Figure 4B:
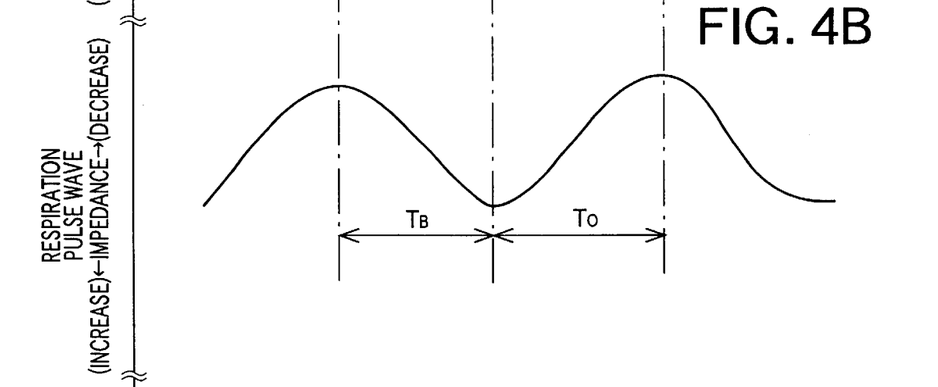
FIG. 4B is a graph showing a respiration pulse wave which is included in the thoracic-impedance pulse wave.
Figure 4C:
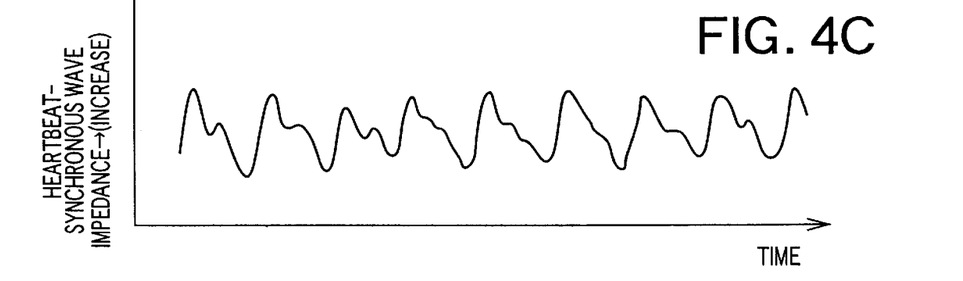
FIG. 4C is a graph showing a heartbeat-synchronous wave which is included in the thoracic-impedance pulse wave.

An inspiration-expiration judging means 62 iteratively judges, based on the respiration pulse wave extracted by the respiration-pulse-wave extracting means 60, whether the subject 14 is in an inspiring state or an expiring state. In the inspiring state of the subject 14, the volume of the thorax of the subject 14 increases and accordingly the thoracic-impedance signal SI detected from the subject 14 increases. Therefore, the inspiration-expiration judging means 62 judges, as the inspiring state of the subject 14, a time interval in which the impedance signal SI increases. FIG. 4B shows a time interval corresponding to an inspiring state of the subject 14, i.e., an inspiring-state interval $T_B$ between a peak point (i.e., maximum point) of each respiration-synchronous pulse and a rising point (i.e., minimum point) of the following respiration-synchronous pulse; and an expiring-state interval $T_O$ between a rising point and a peak point of each respiration-synchronous pulse, in which the impedance signal SI decreases.

A waveform-process-interval determining means 64 identifies a prescribed point of a first half portion of each of the successive T-waves of the electrocardiogram signal SE detected by the electrocardiograph 24, and determines, based on the thus identified point of the first half portion of each T-wave, a start point of a prescribed waveform-process interval (e.g., a constant interval of from 0.2 to 0.3 second, or an interval determined based on a pulse period of the subject 14 (e.g., one fourth of the pulse period)), so that a differentiating-smoothing means 66 processes only respective lengths of the waveform of the heart-sound signal SH that are detected by the microphone 12 in the respective inspiring-state intervals $T_B$ iteratively judged by the inspiration-expiration judging means 62 and simultaneously in the respective waveform-process intervals iteratively determined by the waveform-process-interval determining means 64. The prescribed point of first half portion of each T-wave may be a rising point or a peak point of each T-wave, and the start point of each waveform-process interval may be a time when the prescribed point is detected, or a time which is a small time after the time when the prescribed point is detected.

As shown in FIG. 2, a second heart sound II normally occurs within 0.04 second before or after the terminal end of each T-wave of the electrocardiogram signal SE. Therefore, the length of the heart-sound signal SH detected in each of the iteratively determined waveform-process intervals includes one second heart sound II having the component IIA as its first identifiable change. Though a plurality of heartbeats occur in each inspiring-state interval $T_B$, the component IIA and the component IIP are most largely separated from each other at the terminal end portion of the each inspiring-state interval $T_B$. Therefore, it is preferred that a waveform-process interval be determined based on only the last one of the T-waves detected in the each inspiring-state interval $T_B$. However, it is possible that a waveform-process interval be determined based on each of all the T-waves detected in the each inspiring-state interval $T_B$, or each of a predetermined number of T-waves detected in the each inspiring-state interval $T_B$.

A differentiating-smoothing means 66 differentiates, and thereby smoothes, the respective lengths of the waveform of the heart-sound signal SH that are detected by the microphone 12 in the waveform-process intervals iteratively determined by the waveform-process-interval determining means 64. In the differentiating-smoothing process, each of data points of the heart-sound signal SH that are sequentially input is differentiated by obtaining a linear sum of central differences, according to the following expression (1) pre-stored in the ROM 48:

$$y_{(k)} = d/2 \cdot \sum_{n=1}^{N} C_n \{x_{(k+n)} - x_{(k-n)}\} \quad (1)$$

where d is a value determined based on a sampling period T; N is a degree; and $C_n$ is a coefficient.

Figure 5A:
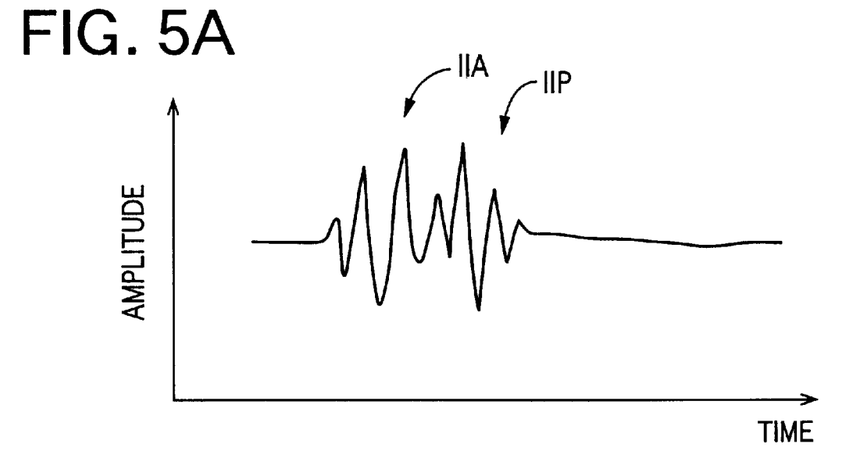
FIG. 5A is a graph showing a heart-sound waveform which is detected by a heart-sound microphone of the system of FIG. 1.
Figure 5B:
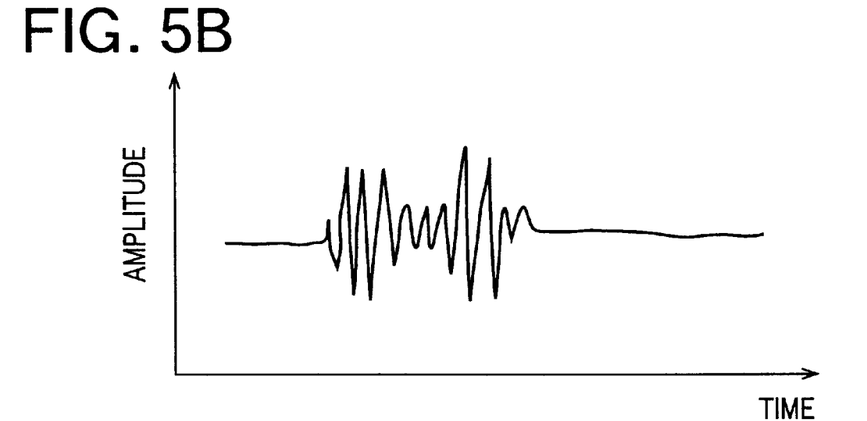
FIG. 5B is a graph showing a waveform which is obtained by smoothing, by differentiation, the waveform shown in FIG. 5A.

For example, d=1/T, N=1, and $C_1$=1. The above expression (1) indicates that the differentiating-smoothing process consists of only low-degree adding and subtracting calculations. Since this process is widely applicable, it is known as a useful process for dealing with a signal obtained from a living subject. FIG. 5A shows a waveform of the heart sounds detected by the microphone 12, before being subjected to the differentiating-smoothing process; and FIG. 5B shows a waveform which is provided by the differentiating-smoothing means 66 by smoothing, by differentiation, the waveform shown in FIG. 5A.

Figure 5C:
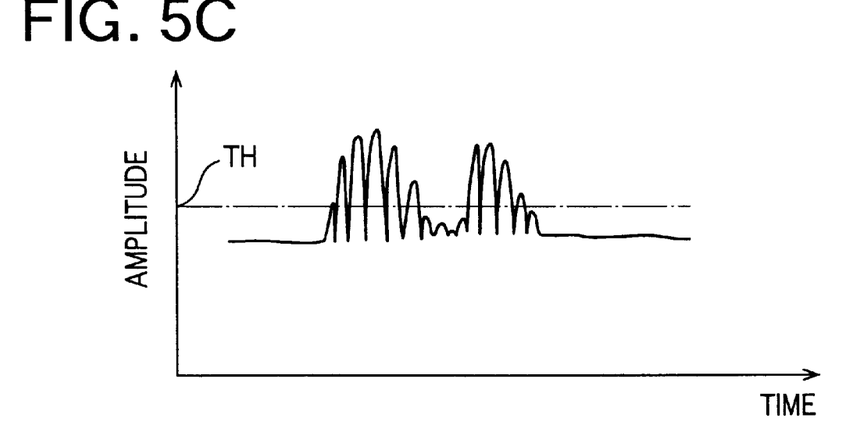
FIG. 5C is a graph showing a waveform which is obtained by squaring the waveform shown in FIG. 5B.

A squaring means 68 determines respective amplitudes or magnitudes of data points of the waveform, smoothed by the differentiating-smoothing means 66, with respect to a base line of the waveform, and squares the respective amplitudes of the data points. FIG. 5C shows a waveform which is provided by the squaring means 68 by squaring the amplitudes of the waveform shown in FIG. 5B. The base line of the waveform, shown in FIG. 5B, indicates a level of the heart-sound signal SH when no heart sounds are detected by the microphone 12. The heart-sound signal SH output from the microphone 12 is an alternating waveform having positive amplitudes and negative amplitudes on both sides of its base line. Accordingly, the differentiated waveform provided by the differentiating-smoothing means 66 is also an alternating waveform having positive and negative amplitudes on both sides of its base line. Since the amplitudes of the alternating waveform may increase on each of the positive and negative sides of the base line, it is not so easy to determine, based on the alternating waveform, a timing when the aortic valve closes. Hence, the alternating waveform is subjected to the squaring process so as to provide a waveform having amplitudes on only the positive side of its base line. In addition, since the components resulting from the heart sounds have amplitudes greater than that of noise, a difference between the respective amplitudes of the components resulting from the heart sounds and the amplitude of noise is amplified by the squaring process. Thus, the waveform provided by the squaring means 68 shows a clear point indicating a timing when the aortic valve closes.

An aortic-valve-closing-timing determining means 70 determines, based on the waveform squared by the squaring means 68, a timing when the aortic valve of the heart of the subject 14 closes. As described previously, the first identifiable change of a length of the heart-sound signal SH that is detected in each waveform-process interval is a component IIA of a second heart sound II. Therefore, for example, the determining means 70 determines, as a timing when the aortic valve closes, a time corresponding to a point on the squared waveform where the respective amplitudes or magnitudes of data points of the squared waveform first exceed a prescribed threshold value TH after the start point of the each waveform-process interval. Alternatively, the determining means 70 may determine, as a timing of closure of the aortic valve, a time corresponding to the first maximum point on the squared waveform, i.e., a peak point of a component IIA. In each case, the determining means 70 starts, at the start point of each waveform-process interval, an judging operation in which the means 70 judges whether the squared waveform has exceeded the prescribed threshold value TH or whether the squared waveform has shown the first maximum point. Thus, the start point of each waveform-process interval is a start point or time when the determining means 70 starts its judging operation, i.e., its aortic-valve-closing-timing determining operation.

A pulse-wave-propagation-velocity-relating-information obtaining means 72 includes a pulse-wave-propagation-time determining means which iteratively determines a time difference between the timing of closure of the aortic valve, determined by the aortic-valve-closing-timing determining means 70, and a timing when a prescribed point (e.g., rising point or peak point) of the photoelectric pulse wave is detected by the photoelectric-pulse-wave sensor 28, as a propagation time DT (second) which is needed for the pulse wave to propagate from the aortic valve to a position where the sensor 28 is worn on the subject 14. The information obtaining means 72 iteratively calculates, based on each of the pulse-wave propagation time values DT iteratively determined by the pulse-wave-propagation-time determining means, a pulse-wave propagation velocity PWV (m/sec) at which the pulse wave propagates through an artery of the subject 14, according to the following expression (2) pre-stored in the ROM 48:

$$PWV = L/DT \quad (2)$$

where L (m) is the propagation distance from the initial portion of the aorta to the position where the sensor 28 is worn.

In the above expression (2), L is a constant which is experimentally obtained in advance. The information obtaining means 72 iteratively operates the display device 52 to display iteratively each of the pulse-wave propagation velocity values PWV determined thereby.

Figure 6:
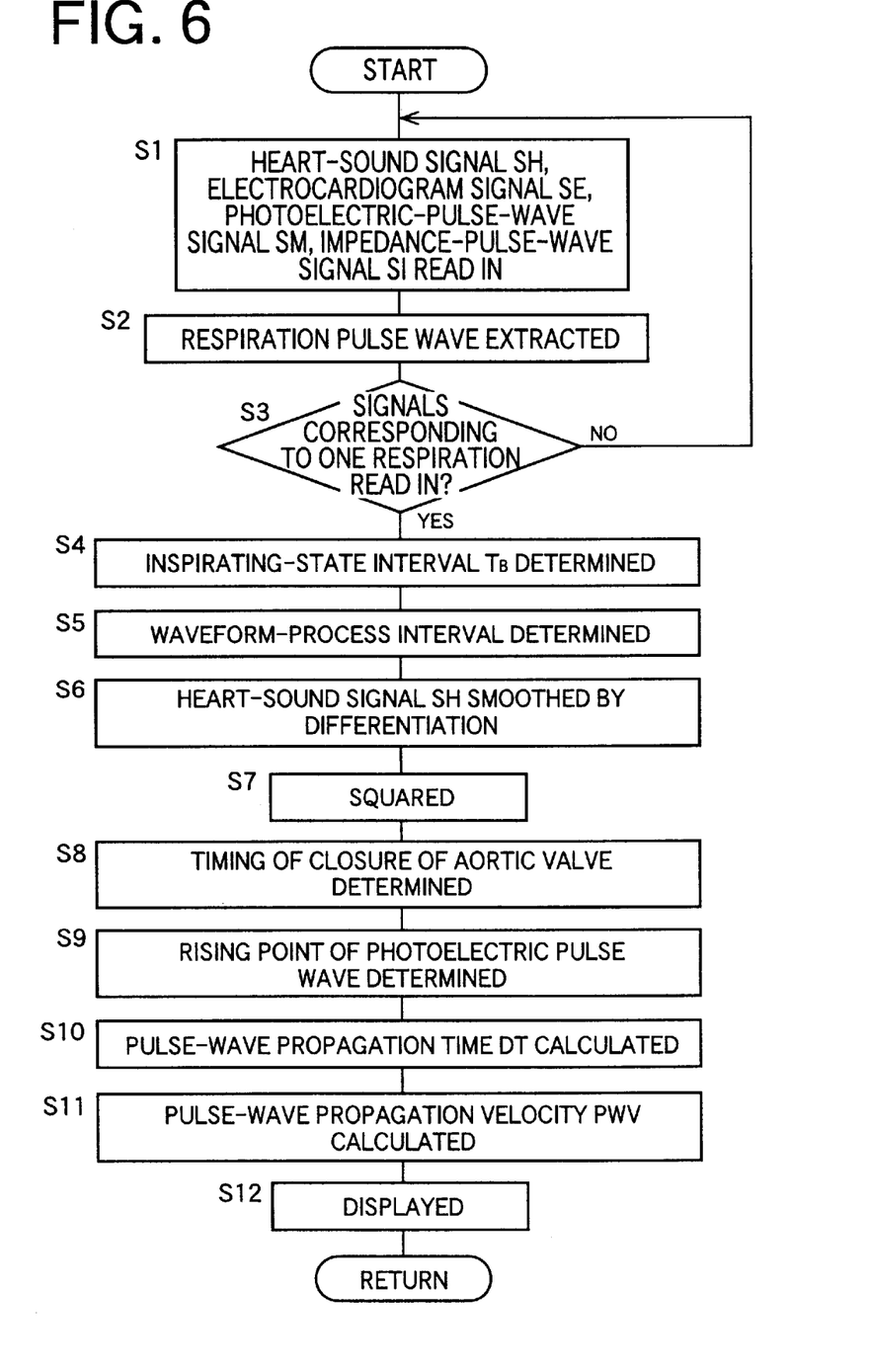
FIG. 6 is a flow chart representing a control program according to which the control device shown in the block diagram of FIG. 3 controls the system of FIG. 1.

FIG. 6 is a flow chart for explaining the essential functions of the control device 20, illustrated in the block diagram of FIG. 3. A control routine according to this flow chart is started when the push button 44 is pushed and a start signal SS is supplied from the button 44 to the control device 20.

In FIG. 6, at Step S1 (hereinafter, Step is omitted), the control device 20 reads in the heart-sound signal SH supplied from the microphone 12, the electrocardiogram signal SE supplied from the electrocardiograph 24, the photoelectric-pulse-wave signal SM supplied from the photoelectric-pulse-wave sensor 28, and the thoracic-impedance signal SI supplied from the thoracic-impedance detecting device 32.

Subsequently, at S2 corresponding to the respiration-pulse-wave extracting means 60, the control device 20 extracts, from the thoracic-impedance signal SI read in at S1, shown in FIG. 4A, an alternating component having frequencies in a frequency band of from 0.1 to 0.5 Hz, and provides a respiration pulse wave, shown in FIG. 4B.

Then, at S3, the control device 20 judges, based on the respiration pulse wave extracted at S2, whether the control device 20 has already read in, at S1, respective lengths of the heart-sound signal SH, the electrocardiogram signal SE, the photoelectric-pulse-wave signal SM, and the thoracic-impedance signal SI that correspond to one-time respiration of the subject 14. If a negative judgment is made at S3, S1 and the following steps are repeated to continue reading in the heart-sound signal SH, the electrocardiogram signal SE, the photoelectric-pulse-wave signal SM, and the thoracic-impedance signal SI, and extracting the respiration pulse wave.

On the other hand, if a positive judgment is made at S3, the control of the control device 20 proceeds with S4 corresponding to the inspiration-expiration judging means 62, where the control device 20 determines a peak point of the current respiration-synchronous signal extracted at S2, and a rising point of the following respiration-synchronous signal (i.e., the terminal end of the current respiration-synchronous signal), and determines a time interval between the peak point and the rising point, as an inspiring-state interval $T_B$.

Then, at S5 corresponding to the waveform-process-interval determining means 64, the control device 20 determines, as the start point of a waveform-process interval, a peak point of the last one of the T-waves of the electrocardiogram signal SE that were detected and read in at S1 in the inspiring-state interval $T_B$ determined at S4. The waveform-process interval lasts for a prescribed time duration (e.g., 0.2 second).

Subsequently, at S6 corresponding to the differentiating-smoothing means 66, the control device 20 replaces the variables $x_{(k+n)}$, $x_{(k-n)}$ of the expression (1), with the data points of a length of the heart-sound signal SH, read in at S1, S2, and S3, which length was read in in the waveform-process interval determined at S5, and thereby differentiates or smoothes the length of the signal SH. Thus, the differentiated waveform of the signal SH is provided. In the expression (1), for example, d, N, and $C_n$ is such that d=1/T, N=1, and $C_1$=1.

Subsequently, at S7 corresponding to the squaring means 68, the control device 20 squares the respective amplitudes of respective data points of the differentiated or smoothed waveform obtained at S6. More specifically described, the control device 20 squares the respective amplitudes of respective data points of the smoothed waveform that are determined with respect to the base line of the waveform.

Then, at S8 corresponding to the aortic-valve-closing-timing determining means 70, the control device 20 determines, as a timing of closure of the aortic valve, a time corresponding to a point on the squared waveform, obtained at S7, where the respective amplitudes or magnitudes of data points of the waveform first exceed a prescribed threshold value TH after the start point of the waveform-process interval.

Then, at S9, the control device 20 determines, based on the photoelectric-pulse-wave signal SM read in at S1, a timing when a rising point of the photoelectric pulse wave is detected by the photoelectric-pulse-wave sensor 28. S9 is followed by S10, S11, and S12 corresponding to the pulse-wave-propagation-velocity-relating-information obtaining means 72.

First, at S10, the control device 20 determines, as a pulse-wave propagation time DT, a time difference between the timing of closure of the aortic valve determined at S8 and the timing of detection of the rising point of the photoelectric pulse wave determined at S9. S10 is followed by S11 where the control device 20 replaces the variable DT of the expression (2), with the pulse-wave propagation time DT determined at S10, and thereby calculates a pulse-wave propagation velocity PV. S11 is followed by S12 where the control device 20 operates the display device 52 to display the pulse-wave propagation velocity PWV calculated at S11. Then, SI and the following steps are repeated, while a timing of closure of the aortic valve is iteratively determined, and a pulse-wave propagation velocity PWV is iteratively calculated based on each of the iteratively determined timings of closure of the aortic valve.

In the embodiment illustrated by reference to the flow chart of FIG. 6, the control device 20 iteratively judges, at S4 (the inspiration-expiration judging means 62), whether the subject 14 is in an inspiring state or not, based on the thoracic-impedance signal SI detected by the thoracic-impedance detecting device 32, and determines, at S8 (the aortic-valve-closing-timing determining means 70), a timing of closure of the aortic valve, based on a second heart sound II detected when the subject 14 is in the inspiring state. Thus, the present system 10 can accurately and iteratively determine a timing of closure of the aortic valve of the subject 14, without needing to force the subject 14 to control his or her respiration.

In addition, in the embodiment illustrated by reference to the flow chart of FIG. 6, the control device 20 iteratively determines, at S8 (the aortic-valve-closing-timing determining means 70), a timing of closure of the aortic valve, based on the last one of the second heart sounds II detected by the microphone 12 in each inspiring-state interval $T_B$ in which the subject 14 is judged as being in the inspiring state at S4 (the inspiration-expiration judging means 62). Thus, the present system 10 can more accurately determine a timing of closure of the aortic valve.

In addition, in the embodiment illustrated by reference to the flow chart of FIG. 6, the control device 20 differentiates and thereby smoothes, at S6 (the differentiating-smoothing means 66), the waveform of the second heart sound II detected by the microphone 12, and provides a smoothed waveform of the second heart sound II in the form of a differentiated waveform showing a clear amplitude change. In addition, the control device 20 squares, at S7 (the squaring means 68), the respective amplitudes or magnitudes of data points of the waveform, processed at S6 (the differentiating-smoothing means 66), which amplitudes are determined with respect to the base line of the waveform, and provides a waveform having amplified amplitudes on only the positive side of its base line. And, at S8 (the aortic-valve-closing-timing determining means 70), the control device 20 determines a timing of closure of the aortic valve, based on the waveform processed at S7 (the squaring means 68). Therefore, the present system 10 can more accurately determine a timing of closure of the aortic valve.

In addition, in the embodiment illustrated by reference to the flow chart of FIG. 6, the control device 20 determines, at S8 (the aortic-valve-closing-timing determining means 70), a timing of closure of the aortic valve in each waveform-process interval whose start point corresponds to the peak point of each T-wave of the electrocardiogram signal SE. Accordingly, the first identifiable change of the heart-sound signal SH after the start point of each waveform-process interval is a component IIA of a second heart sound II. Thus, the present system 10 does not erroneously determine a different change of the signal SH, as a component IIA, and accordingly can more accurately determine a timing of closure of the aortic valve.

In addition, in the embodiment illustrated by reference to the flow chart of FIG. 6, the pulse-wave-propagation-velocity-relating-information obtaining system 10 functions as a heart-sound analyzing apparatus. In other words, a heart-sound analyzing apparatus is employed in the system 10. Therefore, at S8 (the aortic-valve-closing-timing determining means 70), a timing of closure of the aortic valve is accurately determined, and at S11 (the pulse-wave-propagation-velocity-relating-information obtaining means 72), a pulse-wave propagation velocity is accurately determined based on a time difference between the accurately determined timing of closure of the aortic valve and the timing when the prescribed point of the photoelectric-pulse-wave signal SM is detected by the photoelectric-pulse-wave sensor 28.

While the present invention has been described in detail in its embodiment, by reference to the drawings, the invention may otherwise be embodied.

For example, the microphone 1 employed in the pulse-wave-propagation-velocity-relating-information obtaining system 10 is of acceleration type. However, the microphone 1 may be any other sort of microphone, such as airborne type, pendent type, or placement type.

In addition, in the illustrated embodiment, the thoracic-impedance detecting device 32 is employed as a respiration-synchronous-signal detecting device. However, it is possible to employ any other sort of respiration-synchronous-signal detecting device which detects a respiration-synchronous signal; such as a different device commonly used as a respiration-rate meter, than the thoracic-impedance detecting device 32, a device which measures a concentration of carbonic-acid gas contained in expired gas, or a flow meter which measures a flow rate of each of inspired and expired gases. The different device commonly used as the respiration-rate meter may be a device which includes a thermister adapted to be inserted in nose or mouth and detects a change of temperature detected by the thermister; a device which includes a rubber tube filled with electrolytic solution or carbon and adapted to be wound around thorax and measures a change of resistance of the rubber tube; or a device which includes two coils adapted to be placed in front of, and in rear of, thorax and measures a mutual induction caused by a high-frequency wave applied thereto.

In addition, in the illustrated embodiment, only the respective lengths of the heart-sound signal SH that are detected in the waveform-process intervals determined by the waveform-process-interval determining means 64 are subjected to the differentiating-smoothing process and the squaring process. However, it is possible to subject the entire length of the heart-sound signal SH continuously detected by the microphone 12, to the differentiating-smoothing and squaring processes. In the latter case, the single waveform-process interval is the single, aortic-valve-closing-timing-determine interval.

In addition, in the illustrated embodiment, the waveform-process-interval determining means 64 determines, based on the electrocardiogram signal SE, the start point of each waveform-process interval and the start point of each timing-determine interval. However, it is possible to determine the start point of each waveform-process interval or the start point of each timing-determine interval, based on each first heart sound I included in the heart-sound signal SH. For example, it is possible to determine, as the start point of each waveform-process interval or the start point of each timing-determine interval, a time which is subsequent to a time of detection of a maximum amplitude of each first heart sound I, by a time duration equal to one fourth of a pulse period of the subject 14. In the latter case, the electrodes 22 and the electrocardiograph 24 may be omitted.

In addition, in the illustrated embodiment, the differentiating-smoothing means 66 smoothes, by differentiation, the waveform of the heart-sound signal SH, and the squaring means 68 squares the respective amplitudes of data points of the smoothed waveform. However, one or both of the differentiating-smoothing means 66 and the squaring means 68 may be omitted.

The pulse-wave-propagation-velocity-relating-information obtaining system 10 may additionally employ a high-pass filter which is provided between the microphone 12 and the electronic control device 20 and which passes only a component having frequencies in a prescribed pass-frequency range whose lower limit is lower by a prescribed value (e.g., from 0 to 20 Hz) than the lowest frequency of second heart sound II. In this case, since the high-pass filter removes the low-frequency noise (mainly, internal noise such as blood-flow sound) mixed with the heart-sound signal SH, the system 10 can accurately determine a timing of closure of the aortic valve.

In addition, in the illustrated embodiment, the system 10 iteratively determines, based on each of the iteratively determined times of closure of the aortic valve, a pulse-wave propagation time DT and a pulse-wave propagation velocity PWV. Moreover, the system 10 may be so modified as to iteratively calculate, based on each of the iteratively determined pulse-wave propagation times or velocities DT, PWV, a degree of arteriosclerosis of the subject 14 or an estimated blood pressure value of the subject 14.

In addition, in the illustrated pulse-wave-propagation-velocity-relating-information obtaining system 10, the photoelectric-pulse-wave sensor 28 which is worn on an end portion of a finger of the subject 14 is employed as a pulse-wave detecting device. However, a pressure-pulse-wave sensor which is pressed against a prescribed portion of a living subject and detects a pressure pulse wave propagated to the body portion, a pressure-pulse-wave sensor which includes a pressing band adapted to be worn on a prescribed portion (e.g., upper arm) of a living subject and detects a change of a pressure in the pressing band, a photoelectric-pulse-wave detecting probe for use with an oximeter, or an impedance-pulse-wave detecting device which detects an impedance change through electrodes worn on a finger of a living subject may be employed as the pulse-wave detecting device.

It is to be understood that the present invention may be embodied with other changes, improvements and modifications that may occur to one skilled in the art without departing from the spirit and scope of the invention.

What is claimed is:

1. A heart-sound analyzing apparatus, comprising:
   a heart-sound microphone which is adapted to be worn on a living subject to iteratively detect a second heart sound II of the subject;
   a respiration-synchronous-signal detecting device which iteratively detects a respiration-synchronous signal of the subject;
   an inspiration-expiration judging means for judging, based on each of the respiration-synchronous signals iteratively detected by the respiration-synchronous-signal detecting device, whether the subject is in an inspiring state or in an expiring state; and
   an aortic-valve-closing-timing determining means for iteratively determining a timing when an aortic valve of a heart of the subject closes, based on each of a plurality of second heart sounds II which are iteratively detected by the heart-sound microphone in a plurality of time intervals, respectively, in each of which the subject is judged as being in the inspiring state by the inspiration-expiration judging means.

2. An apparatus according to claim 1, wherein the aortic-valve-closing-timing determining means determines a timing when the aortic valve closes, based on a last one of a plurality of second heart sounds II which are detected by the heart-sound microphone in each of the plurality of time intervals in each of which the subject is judged as being in the inspiring state by the inspiration-expiration judging means.

3. An apparatus according to claim 1, further comprising:
a smoothing means for smoothing, by differentiation, a waveform of the second heart sounds iteratively detected by the heart-sound microphone; and
a squaring means for squaring respective amplitudes of a plurality of data points on the smoothed waveform that are determined with respect to a base line of the smoothed waveform,
wherein the aortic-valve-closing-timing determining means iteratively determines a timing when the aortic valve closes, based on the amplitudes squared by the squaring means.

4. An apparatus according to claim 1, further comprising an electrocardiograph which includes a plurality of electrodes adapted to be worn at a plurality of locations on the subject and which detects, through the electrodes, an electrocardiogram of the subject, wherein the aortic-valve-closing-timing determining means comprises means for iteratively determining, based on a prescribed point of each of respective first half portions of a plurality of T-waves of the electrocardiogram detected by the electrocardiograph, a start point of a corresponding one of a plurality of waveform-process intervals in each of which the aortic-valve-closing-timing determining means is to seek a timing when the aortic valve closes.

5. A system for obtaining information relating to a propagation velocity at which a pulse wave propagates along an artery of a living subject, the system comprising:
a heart-sound analyzing apparatus according to claim 1;
a pulse-wave detecting device which is adapted to be worn on the subject to detect the pulse wave which propagates along the artery of the subject; and
a pulse-wave-propagation-velocity-relating-information obtaining means for obtaining said information based on the timing when the aortic valve closes, determined by the aortic-valve-closing-timing determining means of the heart-sound analyzing apparatus, and a timing when a prescribed point of the pulse wave is detected by the pulse-wave detecting device.

6. A system according to claim 5, wherein the pulse-wave-propagation-velocity-relating-information obtaining means comprises a pulse-wave-propagation-time determining means for determining, based on the timing when the aortic valve closes, and the timing when the prescribed point of the pulse wave is detected by the pulse-wave detecting device, a propagation time needed for the pulse wave to propagate from the aortic valve to a position where the pulse-wave detecting device is worn on the subject.

7. A system according to claim 5, further comprising an output device which outputs the information obtained by the pulse-wave-propagation-velocity-relating-information obtaining means, so that an observer can see the output information.

* * * * *